United States Patent [19]

Higdon

[11] Patent Number: 5,298,225

[45] Date of Patent: *Mar. 29, 1994

[54] DETACHABLE COLUMN CARTRIDGE GAS CHROMATOGRAPH

[75] Inventor: William R. Higdon, Pleasanton, Calif.

[73] Assignee: Microsensor Technology, Inc., Fremont, Calif.

[*] Notice: The portion of the term of this patent subsequent to Aug. 17, 1993 has been disclaimed.

[21] Appl. No.: 100,022

[22] Filed: Jul. 30, 1993

Related U.S. Application Data

[63] Continuation-in-part of Ser. No. 812,532, Dec. 23, 1991, Pat. No. 5,236,668.

[51] Int. Cl.⁵ .................................. G01N 30/54
[52] U.S. Cl. .................................. 422/89; 73/23.35; 73/23.39; 73/23.42; 436/161; 96/104; 96/106
[58] Field of Search ............... 422/70, 89; 436/161; 73/23.35, 23.39, 23.42, 61.52, 61.53, 61.56; 210/198.2, 696; 96/104, 106

[56] References Cited

U.S. PATENT DOCUMENTS

| Re. 31,974 | 8/1985 | Brownlee . | |
| 3,213,596 | 10/1965 | Gill . | |
| 3,878,099 | 4/1975 | Ogle | 210/198.2 |
| 3,996,017 | 12/1976 | Kaiser | 73/23.35 |
| 4,083,702 | 4/1978 | Hartigan et al. | 96/106 |
| 4,116,836 | 9/1978 | DeAngelis | 96/106 |
| 4,283,280 | 8/1981 | Brownlee | 210/198.2 |
| 4,289,620 | 9/1981 | Hara | 422/70 |
| 4,451,365 | 5/1984 | Suttler et al. | 96/106 |
| 4,454,749 | 6/1984 | Guillemin et al. | 73/23.42 |
| 4,478,715 | 10/1984 | Goodnight, Jr. | 210/198.2 |
| 4,565,632 | 1/1986 | Hatch et al. | 210/198.2 |
| 4,655,917 | 4/1987 | Shackelford et al. | 210/198.2 |
| 4,669,756 | 6/1987 | Cassaday et al. | 96/106 |
| 4,758,340 | 7/1988 | Marchaud et al. | 96/106 |
| 4,787,656 | 11/1988 | Ryder | 96/106 |
| 4,968,421 | 11/1990 | Spacek et al. | 210/198.2 |
| 4,969,938 | 11/1990 | America | 96/106 |
| 5,105,652 | 4/1992 | Manfredi et al. | 73/23.42 |
| 5,236,668 | 8/1993 | Higdon | 422/89 |

*Primary Examiner*—James C. Housel
*Assistant Examiner*—Jan M. Ludlow
*Attorney, Agent, or Firm*—Skjerven, Morrill, MacPherson, Franklin & Friel

[57] ABSTRACT

A detachable column cartridge for a gas chromatograph is disclosed. The cartridge column contains analytical and reference columns, a heater and a thermocouple, and connects via detachable connectors to a base unit containing an injector, a detector and other components normally found in gas chromatographs. The cartridge arrangement permits a substitute column to be connected to the base unit easily, in the field, when different gases are to be separated and analyzed.

11 Claims, 6 Drawing Sheets

DETACHABLE COLUMN CARTRIDGE GAS CHROMATOGRAPH

RELATED APPLICATION

This application is a continuation-in-part of application Ser. No. 07/812,532, filed Dec. 23, 1991, now U.S. Pat. No. 5,236,668.

FIELD OF THE INVENTION

This invention relates to gas chromatographs and in particular to miniature gas chromatographs having a capillary-type column.

BACKGROUND OF THE INVENTION

In recent years, semiconductor technology has created the possibility of a miniature gas chromatograph. Such a device is described in U.S. Pat. No. 4,474,889, issued to Terry et al., in which the channels for the carrier gas and sample gas are etched in a semiconductor wafer. The analytical column is external to these elements. U.S. Pat. No. 4,471,647, issued to Jerman et al., discloses a miniature gas chromatograph in which all of the channels, including the column, are etched on a semiconductor wafer.

Functionally, a gas chromatograph can be divided into elements which may be used repeatedly, for any tests, and elements which may need to be changed, depending on the gases to be detected. The former group includes the injector and detector and their associated valves and channels. On the other hand, the column may need to be changed in order to permit the gas chromatograph to analyze a different gas or group of gases.

The miniaturization of gas chromatographs has led to the use of miniaturized capillary columns having internal diameters generally in the range of 100-500 microns. Exchanging a column having these dimensions is no trivial task, and one that normally cannot be performed in the field. Frequently, the chromatograph must be returned to the manufacturer, who severs the connections to the analytical and reference lines at the injector and detector, replaces the column, and then reconnects the column to the injector and the detector. Aligning the tubes on either side of the connection is a delicate operation, and connectors containing ferrules are often used for this purpose. A mismatch or the introduction of a "dead volume" in the connector can create eddy currents and spatial voids which enhance Brownian diffusion, ultimately interfering with the accuracy of the analysis. This process can be time consuming and obviously requires the chromatograph to be removed from service. It also involves some expense and training.

SUMMARY OF THE INVENTION

A gas chromatograph in accordance with this invention includes two units: a base unit which contains injector and detector assemblies, manual controls and a visual display; and a column cartridge which contains capillary-type analytical and reference lines, a heater and a thermocouple. Connections between the column cartridge and the base unit are made with precisely machined connectors which are capable of providing a substantially perfect mating between the capillary tubes on either side of the connector, thereby providing a smooth flow of gases from the injector through the analytical and reference lines to the detector. An electrical connector provides connections for the heater and thermocouple. The cartridge is a completely self-contained unit which can simply be plugged into the base unit. The cartridges are interchangeable and can be replaced easily in the field, thereby eliminating the inconvenience and expense of returning the device to the manufacturer.

DESCRIPTION OF THE INVENTION

Figure 1:
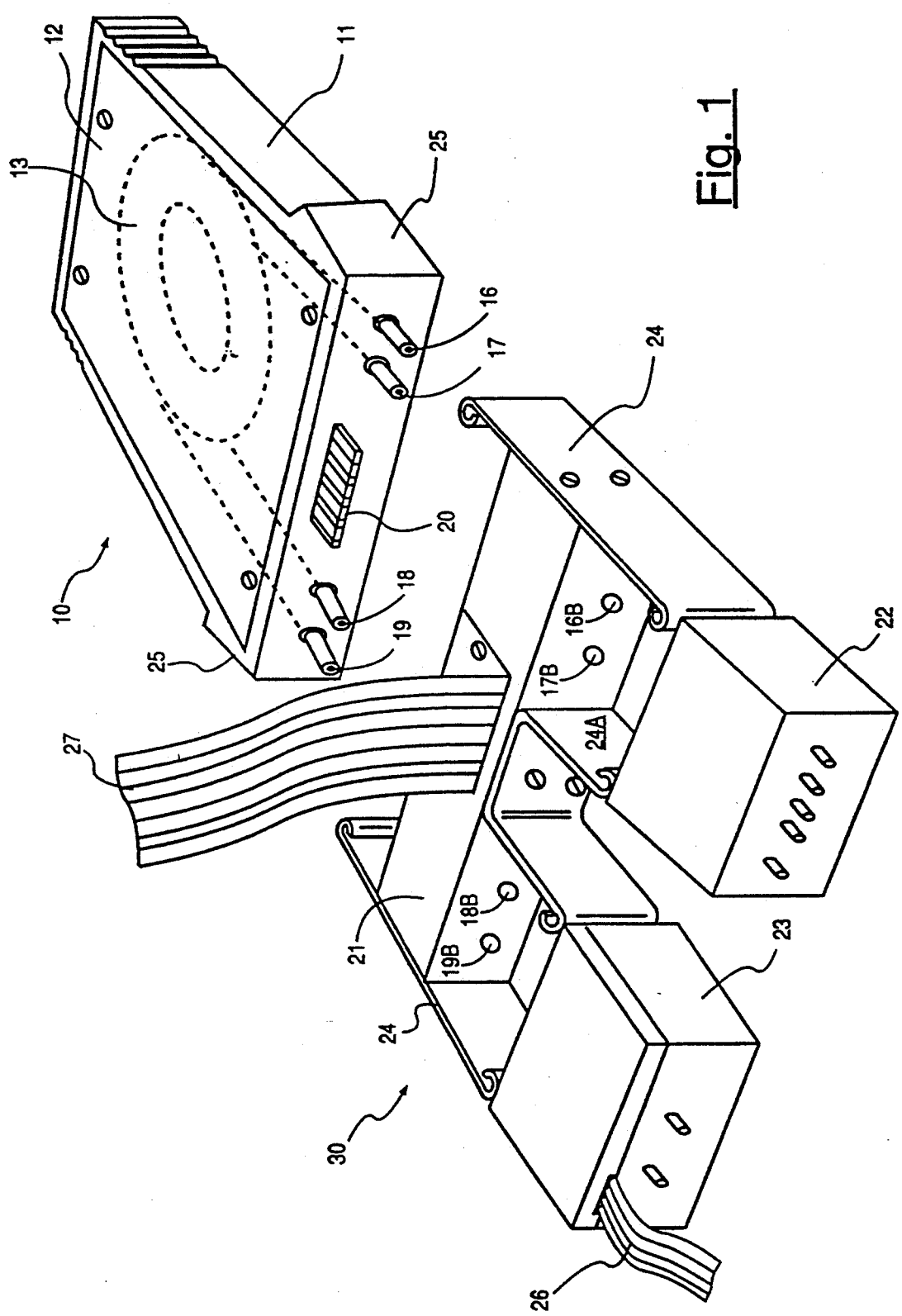
FIG. 1 is an isometric view of a column cartridge and a portion of a base unit in accordance with the invention.

FIG. 1 shows an isometric view of a column cartridge 10. The exterior of column cartridge 10 is formed by a housing 11 and a cover plate 12. A column 13 is placed inside housing 11 and positioned between insulation layers 14 (see FIG. 2B). Adjacent column 13 is a heater 15, which can more easily be viewed in FIG. 2A. The analytical and reference lines of column 13 terminate in male connectors 16 and 17, respectively, for connecting to an injector, and in male connectors 18 and 19, respectively, for connecting to a detector. A male connector 20 is provided for making the necessary electrical connections to heater 15 and a thermocouple (not shown), which is wound separately but adjacent to heater 15.

Also shown in FIG. 1 are a manifold block 21, a gas injector 22 and a solid state detector 23. Manifold block 21, injector 22 and detector 23 are components of a base unit 30 of a gas chromatograph, which contains manual controls, a visual display, and the other elements common to gas chromatographs (not shown). As indicated in FIG. 1, injector 22 and detector 23 are shown in an exploded view with respect to manifold block 21. In reality, injector 22 and detector 23 are connected with manifold block 21 in the manner described below.

Attached on either side of manifold block 21 are spring-loaded latch clips 24, the forward ends of which are formed so as to mate with detents 25 projecting from the sides of housing 11. Latch clips 24 are made of a spring metal so that cartridge 10 is securely fastened to base unit 30 when clips 24 are engaged with detents 25. The rear ends of latch clips 24 cooperate with a spring-loaded clip 24A to hold injector 22 and detector 23 against manifold block 21.

Figure 2A:
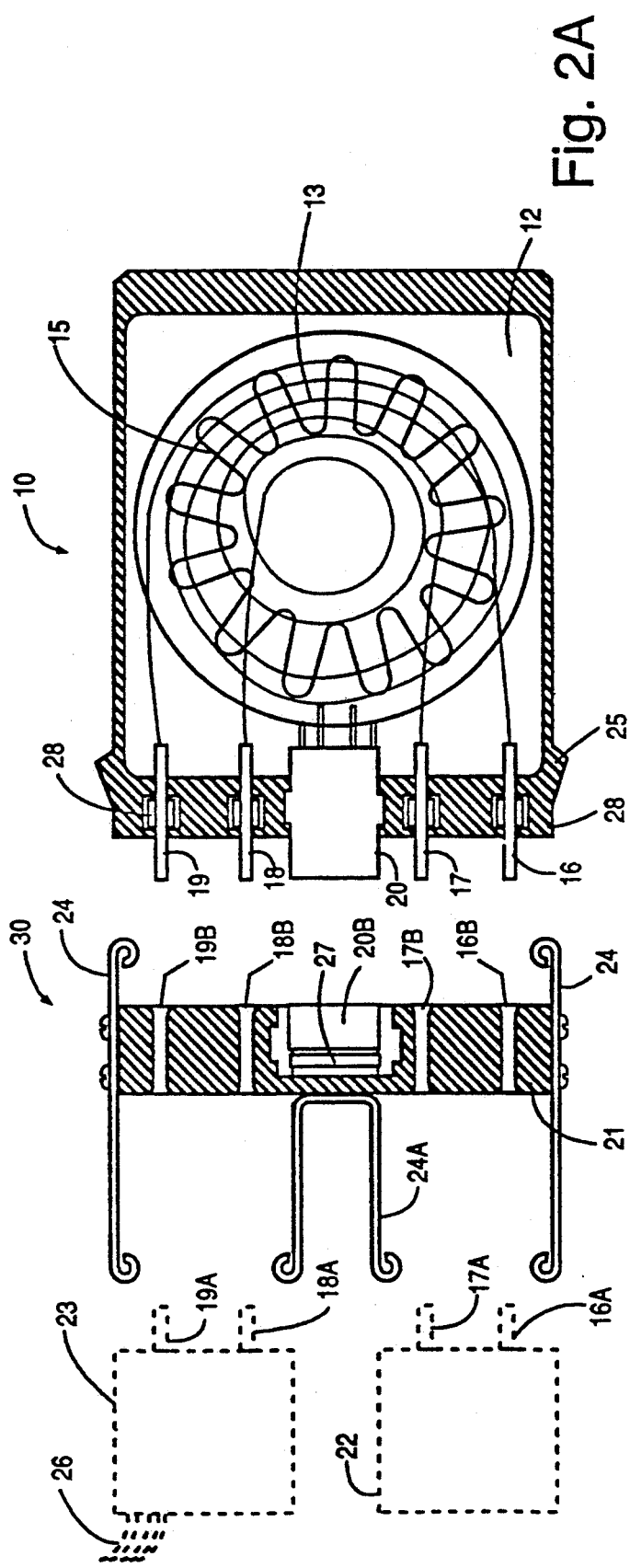
FIGS. 2A and 2B are top and side views, respectively of the column cartridge and base unit elements shown in FIG. 1.
Figure 2B:
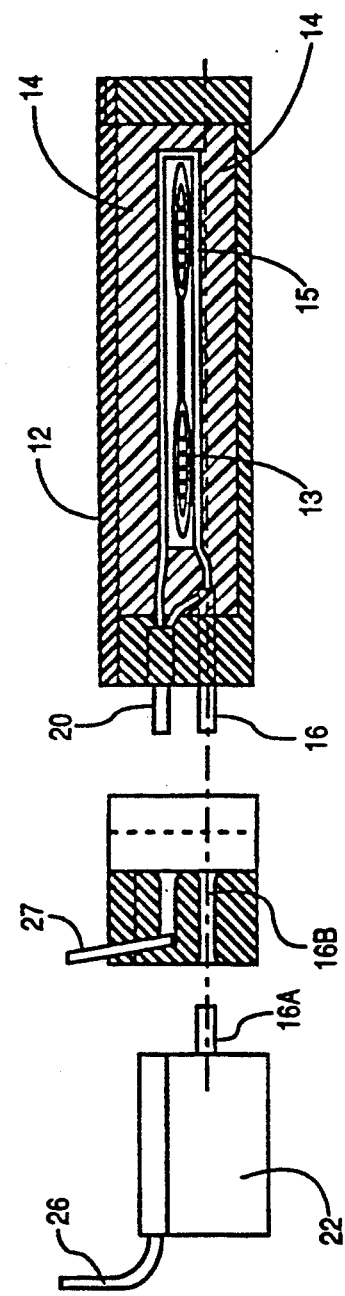

A ribbon-type electrical conductor 26 enters detector 23 from a printed circuit controller board (not shown). A second ribbon-type electrical connector 27 also extends from the printed circuit controller board and connects through manifold block 21 to connector 20. As shown in FIG. 2A, male connector 20 plugs into a female connector 20B in manifold block 21.

Manifold block 21 also contains holes 16B, 17B, 18B and 19B, which extend through the entire width of manifold block 21. Holes 16B-19B are spaced so as to coincide with connectors 16-19, and the diameter of holes 16B-19B is sized so as to allow a snug fit with connectors 16-19. Connectors 16A and 17A on injector 22 and connectors 18A and 19A on detector 23 are likewise spaced and sized so that they may be fitted into the opposite ends of holes 16B-19B.

Connectors 16-19 and 16A-19A are identical with each other. Connectors 16-19 are mounted in cavities 28 of housing 11, and connectors 16A-19A are mounted in similar cavities (not shown) in injector 22 and detector 23.

FIGS. 3 and 4A-4C show in detail how connectors 16-19 and 16A-19A are mounted, using connectors 16 and 16A as an illustration. As noted above, connector 16 is positioned in cavity 28 of housing 11. Similarly, connector 16A is positioned in a cavity 28A in a housing 22A of injector 22.

Figure 3:
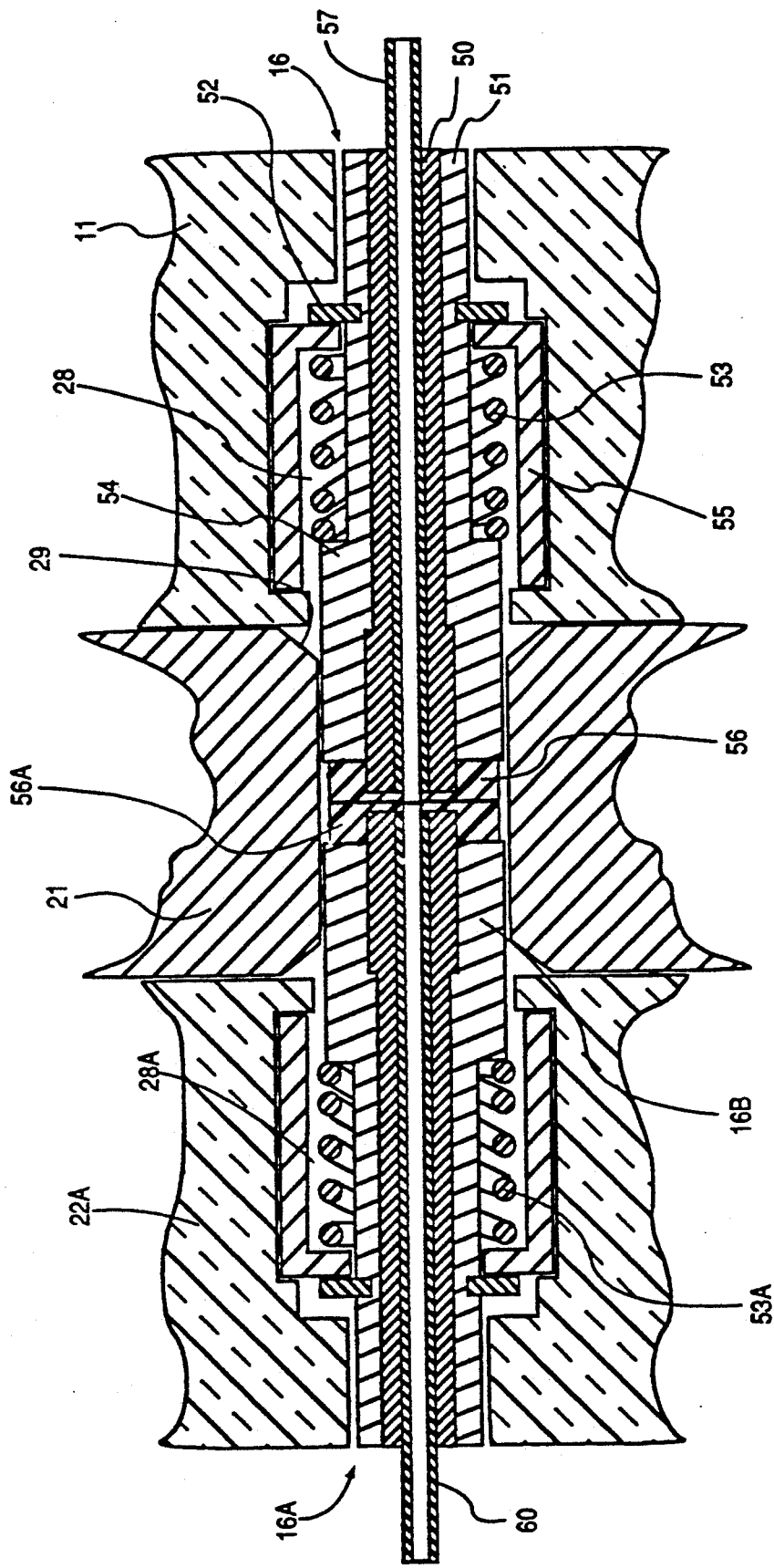
FIG. 3 is a detailed cross-sectional view of a column connector in accordance with the invention.

Since connectors 16 and 16A are identical, only connector 16 will be described in detail. The innermost part of connector 16 consists of a metal insert 50, which is surrounded by a polycarbonate sleeve 51. Sleeve 51 has a notch formed in its exterior circumference into which an C-ring clip 52 is snapped. A compression spring 53 surrounds sleeve 51 and engages a shoulder 54 of sleeve 51, forcing a spring housing 55 against C-ring clip 52. Cavity 28 is formed such that spring housing 55 is held firmly in place, while sleeve 51 and C-ring clip 52 are free to move a short distance to the right, as shown in FIG. 3.

One end of connector 16 projects from cartridge 10 (see FIG. 1) and is inserted into hole 16B in manifold block 21. A conical tapered surface 29 at the outside edge of hole 16B helps to guide connector 16 into hole 16B.

Figure 4A:
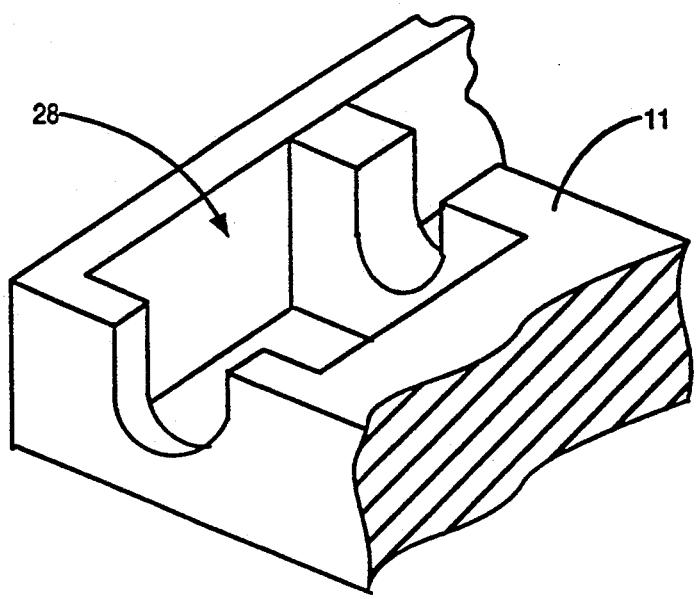
FIG. 4A, 4B and 4C are additional views of the column connector and associated components shown in FIG. 3.
Figure 4B:
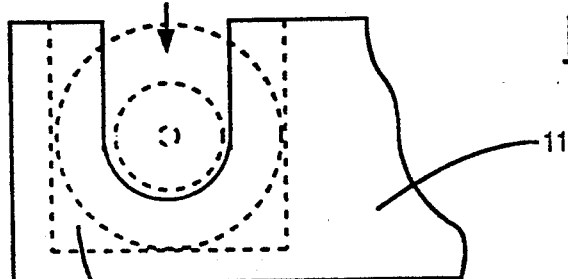
Figure 4C:
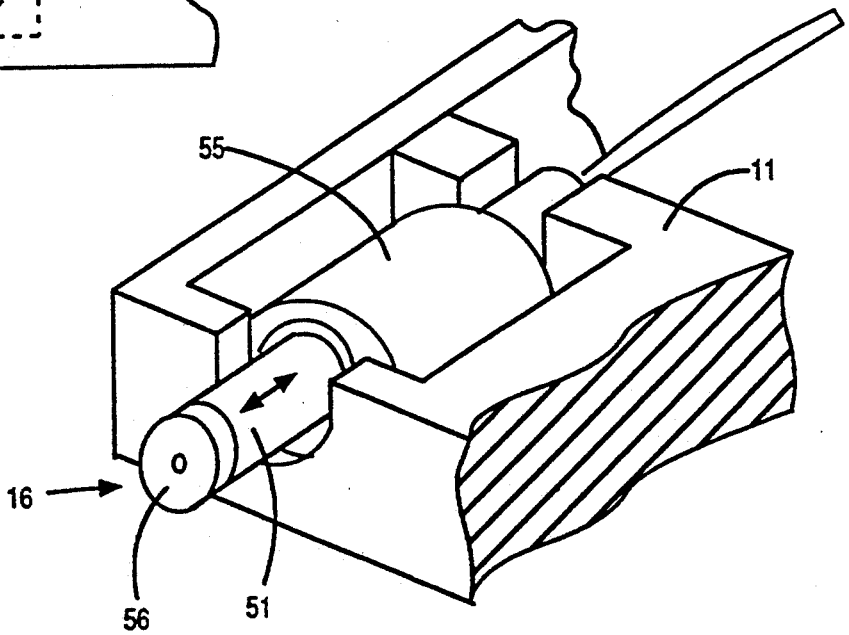

At the end of connector 16 which is inserted into hole 16B, metal insert 50 projects slightly beyond sleeve 51. An elastomeric gasket 56 is fitted over the projecting end of metal insert 50. (The structure of gasket 56 is shown in FIGS. 3 and 4C.) A hole is formed along the axis of metal insert 50, and this hole lines up perfectly with a hole formed in gasket 56 when gasket 56 is fitted over the end of metal insert 50. A polyimide-coated capillary column 57 is inserted into the hole in metal insert 50 until column 57 reaches the end of metal insert 50. Connector 16 is then heated to the melting point of the polyimide, causing the polyimide coating to bond column 57 to metal insert 50. A column 60 is similarly fitted into connector 16A.

As noted above, the structure of connector 16A is identical to that of connector 16. Because injector 22 is attached to manifold block 21, connector 16A is permanently fitted into hole 16B. Connectors 16 and 16A are positioned so that spring 53 and its counterpart spring 53A in connector 16A are compressed slightly when clips 24 engage detents 25, pressing housing 11 against manifold block 21. Accordingly, gasket 56 and its counterpart gasket 56A in connector 16A are compressed against each other forming a seal against the leakage of gas at the point where connectors 16 and 16A make contact.

In manufacturing this structure, it is very important that the axial holes in connectors 16 and 16A be machined accurately so that they are positioned at the axis of each connector. Similarly, the holes in gaskets 56 and 56A must be formed at the precise center of each gasket and must line up perfectly with the holes in connectors 16 and 16A. The holes in connectors 16 and 16A must allow a capillary column (such as column 57) to slide within them while firmly gripping the end of the column when it has been fully inserted. It has been found that this process is facilitated by tapering the holes slightly to a slightly smaller diameter at the end adjacent the elastomeric gasket. This ensures that the ends of columns 57 and 60 will be accurately aligned when cartridge 10 is attached to base unit 30.

Connectors suitable for use in this device are available from Valdor, Inc. of San Jose, Calif.

The structure of connectors 17-19 and 17A-19A is identical to that of connectors 16 and 16A. In a similar manner, they are fitted into holes 17B-19B in such a way that columns inserted into connectors 17-19 are lined up accurately with columns inserted into connectors 17A-19A.

Figure 5:
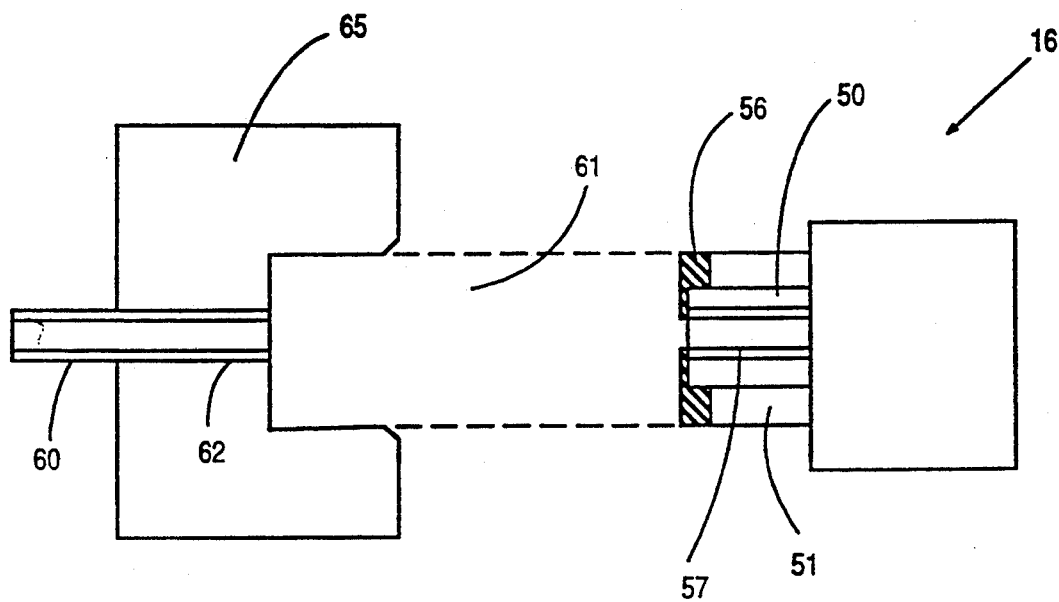
FIG. 5 is an illustration of an alternative embodiment in accordance with the invention.

An alternative structure for the connectors is illustrated in FIG. 5. In this embodiment, connector 16A is omitted, and a cylindrical cavity 61 is formed in a manifold block 65. The outside diameter of sleeve 51 is just slightly smaller than the inside diameter of cavity 61. A hole 62 for connector 60 is bored in manifold block 65, so that the axis of hole 62 and cavity 61 line up perfectly. When connector 16 is inserted into cavity 61, columns 57 and 60 line up perfectly, and gasket 56 is compressed against the rear wall of cavity 61, thereby creating a tight seal.

Figure 6:
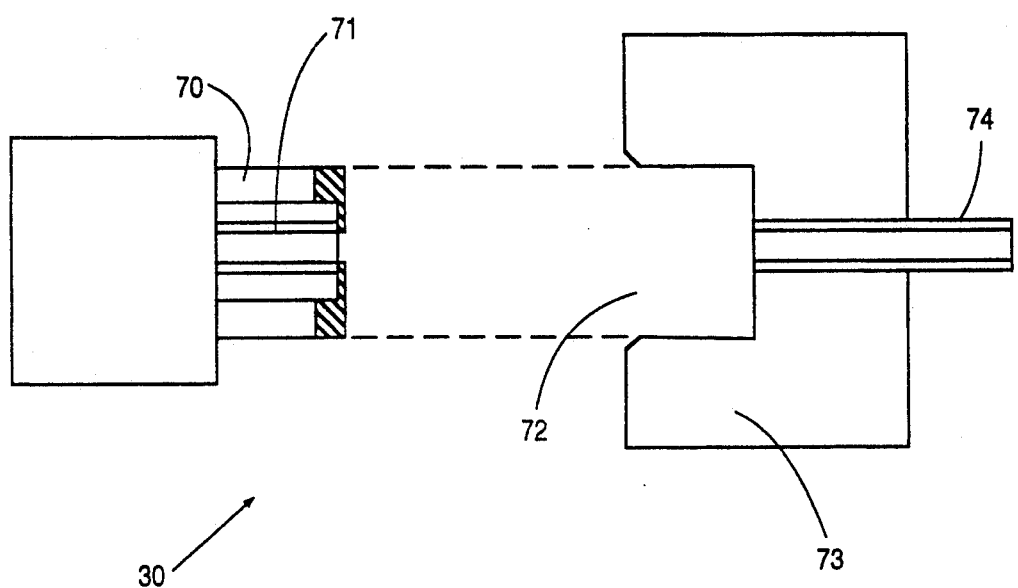
FIG. 6 is an illustration of another embodiment in accordance with the invention.

In another alternative structure the connector and cavity are essentially reversed, the connector being part of the base unit and the cavity being part of a detachable column cartridge. As shown in FIG. 6, a connector 70, which may be similar in every respect to connector 16, projects from base unit 30. A length of capillary tube 71 communicates with, for example, an injector and extends to the end of connector 70. A cavity 72 is formed in a cartridge housing 73, and one end of an analytical column 74 terminates at the rear wall of cavity 72. The other end of column 74 terminates at the rear wall of a similar cavity and forms a connection to a detector. Connector 70 may be spring-loaded in the same manner as connector 16, described above. Base unit 30 and cartridge housing 73 may be detachably connected with spring-loaded latch clips as shown in FIG. 2A.

The foregoing embodiments are intended to be illustrative and not limiting. Numerous other embodiments will be apparent to those skilled in the art. For example, the principles of the invention are applicable to gas chromatographs which do not contain a Wheatstone Bridge type detector and therefore have no need for a reference column. All such alternative embodiments are included within the broad principles of the invention, as defined in the following claims.

I claim:

1. A gas chromatograph including a detachable column cartridge, said gas chromatograph comprising:
   a base unit, said base unit comprising:
   an injector and a detector; and
   a first male connector and a second male connector projecting from said base unit, a first capillary tube extending between said first male connector and said injector and a second capillary tube extending between said second male connector and said detector;
   a detachable column cartridge, said column cartridge comprising;
   a housing including a first cavity and a second cavity, each of said first and second cavities opening to a face of said housing; and a capillary flow channel, said capillary flow channel comprising a capillary column disposed in said housing, said capillary flow channel having a first end which terminates at a rear wall of said first cavity and a second end which terminates at a rear wall of said second cavity, each of said first and second cavities having an internal surface which is sized and shaped so as to provide a sliding fit with an external surface of a corresponding one of said first and second male connectors;

means for attaching said base unit and said column cartridge, said means allowing said column cartridge to be detached from said base unit;

each of said first and second male connectors projecting into a corresponding one of said first and second cavities when said base unit and said column cartridge are attached, said first capillary tube lining up with the first end of said capillary flow channel and said second capillary tube lining up with the second end of said capillary flow channel; and biasing means for maintaining a pressure between the end surfaces of each of said first and second male connectors and the rear walls of said first and second cavities, respectively, when said base unit and said column cartridge are attached, the pressure being sufficient to prevent leakage of a gas flowing through said capillary flow channel and said first and second capillary tubes.

2. The gas chromatograph of claim 1 wherein said means for attaching comprises a spring-loaded element.

3. The gas chromatograph of claim 1 wherein said internal surface comprises a tapered surface for guiding one of said first and second male connectors, respectively, into said cavity.

4. The gas chromatograph of claim 1 wherein each of said male connectors comprises a gasket which forms the end surface of said male connector.

5. The gas chromatograph of claim 4 wherein each of said gasket comprises an elastomeric material.

6. The gas chromatograph of claim 1 wherein each of said male connectors comprises a portion of a capillary tube fitted inside a metal insert.

7. The gas chromatograph of claim 6 wherein the outer surface of the capillary tube inside said metal insert is coated with polyimide.

8. The gas chromatograph of claim 1 wherein said biasing means comprises a compression spring.

9. The gas chromatograph of claim 1 where each of said internal surfaces and said external surfaces is cylindrical.

10. The gas chromatograph of claim 1 wherein said column comprises an analytical column and wherein said column cartridge further comprises a reference column.

11. The gas chromatograph of claim 10 wherein said column cartridge comprises a heater element, said heater element being positioned adjacent said analytical and reference columns.

* * * * *